United States Patent [19]

Higa et al.

[11] Patent Number: 4,772,609

[45] Date of Patent: Sep. 20, 1988

[54] ANTIVIRAL GUANIDINE DERIVATIVES AND COMPOSITIONS THEREFOR

[75] Inventors: Tatsuo Higa, Okinawa, Japan; Ryuichi Sakai, Vero Beach, Fla.

[73] Assignee: Harbor Branch Oceanographic Institution, Inc., Ft. Pierce, Fla.

[21] Appl. No.: 879,079

[22] Filed: Jun. 26, 1986

[51] Int. Cl.$^4$ .................. A61K 31/505; C07D 239/32; C07D 239/42; C07D 239/30

[52] U.S. Cl. .................................... 514/275; 514/272; 544/321; 544/323; 544/330; 544/332

[58] Field of Search ............... 544/321, 323, 330, 332; 514/272, 275

[56] References Cited

U.S. PATENT DOCUMENTS 4,629,729  12/1986  Gatti .................................... 544/330

Primary Examiner—John M. Ford
Assistant Examiner—J. G. Mullins
Attorney, Agent, or Firm—Carroll F. Palmer

[57] ABSTRACT

This invention relates to antiviral organic guanidine derivatives compositions; a process of producing the antiviral compositions; and a method for inhibiting viruses utilizing the compositions. More particularly, the compositions are tubastrines derived from marine coral *tubastrea aurea*.

6 Claims, No Drawings

ANTIVIRAL GUANIDINE DERIVATIVES AND COMPOSITIONS THEREFOR

FIELD OF THE INVENTION

This invention relates to organic compounds which have useful antiviral activity. More particularly, this invention relates to organic guanidine derivative compositions derived from the Coral *Tubastrea aurea* and antiviral methods of using the compositions.

BACKGROUND OF THE INVENTION

Viral diseases inflict man, plants, insects, and animals. The prevention and control of viral diseases have important health and economic implications.

Viral diseases contribute to inflictions in humans including common colds, herpes and cancer and the importance of their control is obvious. Also important is control of viral diseases in animals for economic reasons as well as the ability of such animals to become virus reservoirs or carriers which facilitate the spreading of viral diseases to humans. Viral plant diseases have been known to have a disruptive effect on the cultivation of fruit trees, tobacco, and various vegetables. Insect viral diseases are also of interest because of the insects' ability to transfer viral diseases to humans.

The prevention and control of viral diseases is thus of prime importance to man and considerable research has been devoted to antiviral measures. Certain methods and chemical compositions have been developed which aid in inhibiting, controlling or destroying viruses but additional methods and antiviral chemical compositions are needed.

A potential source for antiviral compositions is marine plant and animal life and of particular interest herein is coral.

Previous work has indicated that marine organisms can be a source for guanadine compositions See L. Chevolet in *Marine Natural Products: Chemical and Biological Perspectives* (ED. P. J. Scheurer), Vol. IV, pp. 54-91, 1981, Academic Press, New York. The entire disclosures of the above-noted literature reference is hereby incorporated herein by reference.

While certain compositions of marine origin have been found, additional useful antiviral compositions are needed.

SUMMARY OF THE INVENTION

It is therefore an object of the invention to provide novel compositions which are useful as antiviral agents; antiviral methods of using the compositions; and a process for producing such compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formulae I-III:

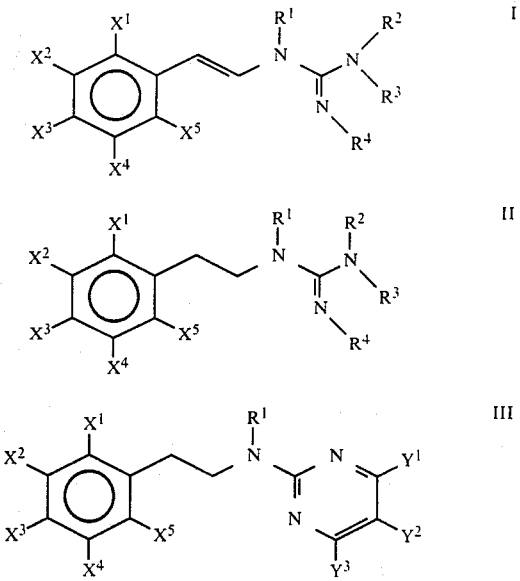

wherein $R^{1-4}$ are the same or different and are a hydrogen, hydroxyl, lower acyl, or lower alkyl group; $X^{1-5}$ and $Y^{1-3}$ are the same or different and are a hydrogen, hydroxyl, thiol, lower alkylthiol, nitro, amino, lower monoalkyl amino, lower dialkyl amino, lower alkylsulfonyl, aminosulfonyl, hydroxysulfonyl ($-SO_3H$), lower acylamino, halogen, lower alkoxy, or lower acyloxy group. The lower acyl, lower alkyl group, lower alkylthiol, lower monoalkyl amino, lower dialkyl amino, lower alkylsulfonyl, lower acylamino, lower alkoxy, and lower acyloxy groups comprise lower organic groups have from 1-5 carbon atoms.

In preferred embodiments of the invention, the composition is substantially pure. In further preferred embodiments the substituent organic groups identified by $R^{1-4}$, are hydrogen or lower alkyl groups having from 1 to 5 carbon atoms, and $X^{1-5}$ and $Y^{1-3}$ are hydrogen, hydroxyl, lower alkoxy or lower acyloxy groups having from 1 to 5 carbon atoms.

In more preferred embodiments of the invention, the invention comprises compositions of formulae IV-VI:

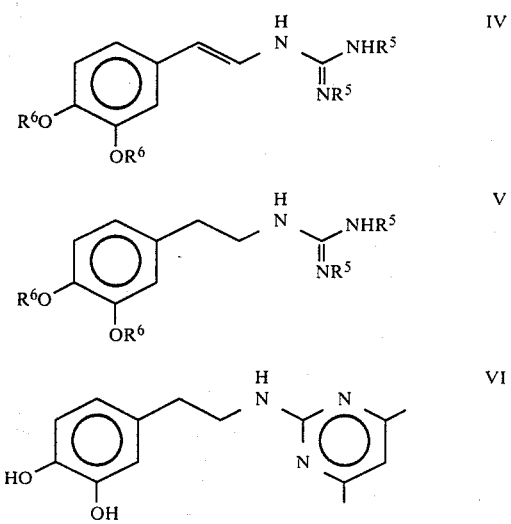

where $R^5$ and $R^6$ are the same or different and are hydrogen or acetyl.

As embodied and fully described herein, the invention also comprises an antiviral composition comprising, as active ingredient, an effective antiviral or amount of one or more compositions according to formulae I-VI.

As embodied and fully described herein, the invention also comprises a process to produce the compositions of formulae I-VI. The process comprises the steps of: collecting Coral *Tubastrea aurea;* contacting the coral with a suitable organic solvent to obtain an extract comprising a composition of formulae I-VI; and isolating a composition according to formulae I-VI from the extract.

In preferred embodiments of the invention the suitable organic solvent is selected from the group consisting of: acetone, ethyl acetate, toluene, methanol, methyl ethyl ketone, ethanol, methyl isobutyl ketone and mixtures thereof. In preferred embodiments isolation of the compositions of the invention is accomplished by partition between aqueous and organic solvents and chromatography methods.

As embodied and fully described herein, the invention further comprises a method for inhibiting viruses comprising contacting a virus with an effective antiviral amount of one or more compositions according to formulae I-VI.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention as embodied and fully described herein, the invention comprises compositions of the general formulae I-III:

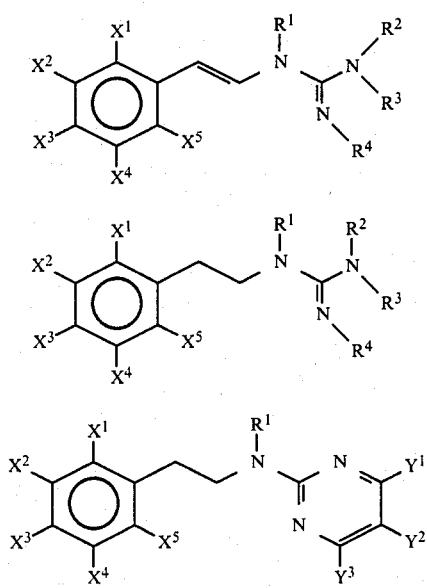

wherein $R^{1-4}$ are the same or different and are a hydrogen, hydroxyl, lower acyl, or lower alkyl group; $X^{1-5}$ and $Y^{1-3}$ are the same or different and are a hydrogen, hydroxyl, thiol, lower alkylthiol, nitro, amino, lower monoalkyl amino, lower dialkyl amino, lower alkylsulfonyl, aminosulfonyl, hydroxysulfonyl ($—SO_3H$), lower acylamino, halogen, lower alkoxy, or lower acyloxy group. The lower acyl, lower alkyl group, lower alkylthiol, lower monoalkyl amino, lower dialkyl amino, lower alkylsulfonyl, lower acylamino, lower alkoxy, and lower acyloxy groups comprise lower organic groups have from 1-5 carbon atoms.

In preferred embodiments of the invention, the composition is substantially pure. In further preferred embodiments the substituent organic groups identified by $R^{1-4}$ are hydrogen or lower alkyl groups having from 1 to 5 carbon atoms and $X^{1-5}$ and $Y^{1-3}$ are hydrogen, hydroxyl, lower alkoxy or lower acyloxy groups having from 1 to 5 carbon atoms.

In more preferred embodiments of the invention, the invention comprises compositions of formulae IV-VI:

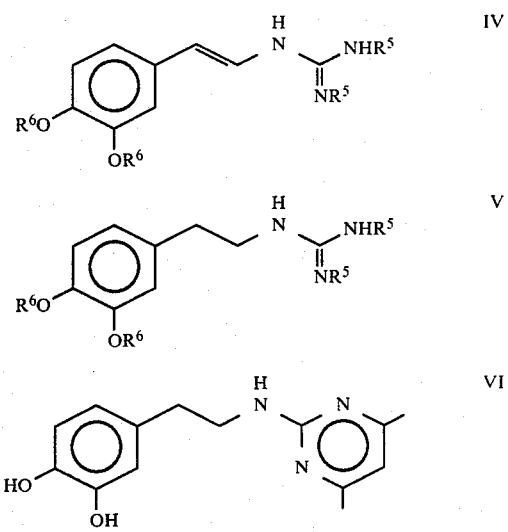

wherein $R^5$ and $R^6$ are the same or different and are hydrogen or acetyl.

In accordance with the invention an antiviral composition is provided comprising as active ingredient an effective antiviral amount of one or more of the compositions described above and identified by formulae I-VI and a non-toxic pharmaceutically acceptable carrier or diluent. Useful examples of non-toxic pharmaceutically acceptable carriers or diluents include, but are not limited to the following: ethanol; dimethyl sulfoxide; and glycerol.

In accordance with the present invention, virus cells are inhibited or killed by a method comprising contacting a virus with an effective antiviral amount of one or more compositions according to unrestricted formula I. The minimal effective amount or dosage required for activity is generally from 5 to 100 micrograms against 25 to 80 plaque forming units of virus cells. The composition of unrestricted formula I-VI are active for inhibiting or killing a diverse range of viruses including, but not limited to, the RNA viruses, vesicular stomatitis (herein "VSV"), arenaviruses, coronaviruses, rhinoviruses, influenza viruses and the DNA viruses, herpes simplex-I (herein "HSV-I"), other herpes viruses, adenoviruses, coxsackie viruses, polioviruses and papovaviruses.

The effectiveness of the compositions of the invention for inhibiting virus cells indicates that the compositions of unrestricted formulae I–VI should also be useful in controlling viral infections in host animals and plants which are caused by a virus which is thus inhibited or destroyed. Viral infections which may be controlled by utilizing compositions of the present invention include, but are not limited to, those caused by those RNA viruses and DNA viruses described above. The invention may also be useful in controlling common viral infections of plants.

As embodied and fully described herein, the invention also comprises a new process to produce the compositions of formulae I–VI. The process comprises the steps of: collecting Coral *Tubastrea aurea;* contacting the coral with a suitable organic solvent to obtain an extract of a composition of formulae I–VI; and isolating a composition according to formulae I–VI from the extract.

A detailed description and explanation of a preferred embodiment of the process of the invention to produce a composition according to formulae I is as follows. A quantity of coral *Tubastrea aurea* is collected at a reef of Onna, Okinawa. The Coral is contacted with a first organic solvent to form an extract. The extract is then concentrated and partitioned between water and a second organic solvent. The aqueous portion or extract which incorporates the desired compositions, is freeze-dried to yield a solid. The solid is extracted with methanol to yield a yellow gum. The gum is removed and subjected to chromatography to obtain a composition according to formulae I–VI.

Acetone is the presently preferred choice for the first solvent, however, other suitable solvents may be substituted for acetone. A suitable first solvent should be capable of solubilizing the coral. Suitable first solvents which may be substituted for acetone include, but are not limited to, the following organic solvents: methyl ethyl ketone; methanol; ethanol; methyl isobutyl ketone, isopropanol and mixtures thereof. Suitable second organic solvents should be capable of extracting and separating out impurities of formulae I–VI or other components from the aqueous solution of compositions. Suitable second solvents which may be substituted for ethyl acetate include, but are not limited to ether; tetrahydrofuran; methylene chloride; chloroform; and mixtures thereof. Different ratios of solvent mixtures may be used for the first and second solvents in the invention as would be known to those skilled in the art.

Any suitable fractionation and isolation techniques may be utilized in accordance with the process of the invention. Suitable fractionation techniques include various chromotography techniques, utilizing, for example columns of silica gel, TSK HW-40 gel and Sephadex LH-20 or high pressure liquid chromatography with a suitable column as would be known to those skilled in the art (e.g., Merck Hibar RP-18 column) eluted with a suitable solvent such as, for example, methanol.

It is therefore apparent that the compositions of the invention, the processes for producing the compositions of the invention and the methods for utilizing the compositions of the invention to inhibit viruses are effective for inhibiting or destroying viruses and therefore controlling diseases caused by or related to such viruses in fulfillment of the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

Preparation of Examples 1–5

Examples 1

Preparation of tubastrine (Composition 1):

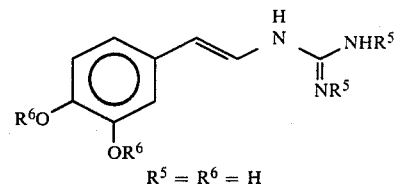

$R^5 = R^6 = H$

Example 1

A specimen (2 kg) of the coral *Tubastrea aurea* WAS collected at a reef of Onna, Okinawa. The fresh material was extracted by steeping in acetone (3 L) for 24 hr. The extract was concentrated and partitioned between ethyl acetate and water. The aqueous solution was freeze-dried yielding a solid which was then extracted with methanol (300 mL) to give 18 gms. of yellow gum having antiviral activity.

A part (9 gms.) of the gum was chromatographed on polystyrene gel by eluting with 50% methanol in water and then with absolute methanol. The latter eluate (2.5 gms.) was passed through a short column of silica gel with a mixture of isopropanol-ethyl acetate-water (5:4:1) to furnish 2.2 gms. of yellow solid. This solid was further separated using TSK HW-40 gel (methanol) and finally Sephadex LH-20 to give 550 mg of tubastrine (1) as a light yellow solid: mp 173°–5°; UV (MeOH) λmax 222 ($\epsilon$14500), 280 sh ($\epsilon$17400), 287 ($\epsilon$18500), and 304 nm ($\epsilon$14300); IR (KBr) 3320, 3130, 1670, 1640, 1600, 1520, 1450, 1350, 1300, 1275, 1190, 1155, 1110, 1010, 955, 870, and 800 cm$^{-1}$; $^1$H NMR (CD$_3$OD) δ6.95 (1H, d, J=13.7 Hz), 6.84 (1H, br s), 6.73 (2H, br s), and 6.17 (1H, d, J=13.7 Hz); $^{13}$C NMR (CD$_3$OD) δ155.9s, 146.5s, 146.2s, 128.7s, 120.0d, 119.2d, 118.5d, 116.5d, and 113.7d; LRFABMS m/z 194 (M$^+$+1).

Example 2

Preparation of tubastrine tetraacetate (Composition 2):

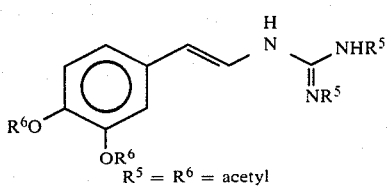

$R^5 = R^6 = $ acetyl

A mixture of tubastrine (1) (8 mg), acetic anhydride (0.1 mL), and pyridine (0.1 mL) was allowed to stand at room temperature for 12 hrs. After adding methanol the solution was concentrated and the residue was purified by HPLC (silica gel, ethyl acetate) to give 5 mg (28.6%) of tubastine tetraacetate (2): mp 148°–150° C.; IR (film) 1770, 1700, 1650, 1600, 1500, 1370, 1310, 1255, 1200, 1170, 1100, 1010, and 895 cm$^{-1}$; UV (MeOH) $\lambda_{max}$ 243 ($\epsilon$15000) and 320 nm ($\epsilon$26000); $^1$H NMR (CDCL$_3$) $\delta$13.1 (1H, br s, NH), 10.7 (1H, d, J=10.4 Hz, NH), 7.65 (1H, dd, J=14.8, 10.4 Hz), 7.22 (1H, dd, J=8.3, 2.0 Hz), 7.12 (1H, d, J=8.3 Hz), 6.17 (1H, d, J=14.8 Hz), 2.30 (3H, s), 2.29 (3H, s), 2.23 (3H, s), and 2.21 (3H,s); $^{13}$C NMR (CDCl$_3$) $\delta$186.3s, 172.7s, 168.2s, 151.9s, 142.3s, 141.0s, 134.7s, 124.1d, 123.6d, 122.9d, 120.4d, 114.4d, 28.7q, 25.1q, 20.6 (2q).

Example 3

Preparation of tubastrine diacetate (Composition 3):

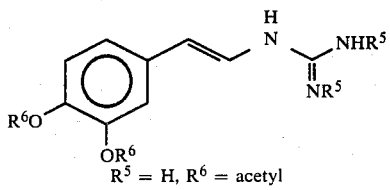

$R^5 = $ H, $R^6 = $ acetyl

To a solution of (1) (5 mg) in 0.2 mL of 3:1 acetic anhydride-methanol was added three drops of pyridine, and the mixture was allowed to stand at room temperature for 25 min. The mixture was concentrated to give 7.5 mg of residue which on recrystallization from heptane-dichloromethane-methanol afforded 5.7 mg of tubastrine diacetate (3): mp 185°–192° C.; UV (MeOH) $\lambda_{max}$ 219 ($\epsilon$12000) and 277 nm ($\epsilon$22000); IR (KBr) 3300, 3150, 1750, 1600 (br), 1500, 1420, 1370, 1260, 1210, 1180, 1140, 1105, 1005, 965, 920, 900, 890, 840, and 740 cm$^{-1}$; $^1$H NMR (CD$_3$OD) $\delta$7.27 (1H, d, J=8.3 Hz), 7.26 (1H, s), 7.21 (1H, d, J=13.9 Hz), 7.13 (1H, d, J=8.3 Hz), 6.27 (1H, d, J=13.9 Hz), 2.26 (3H, s), and 2.25 (3H, s); $^{13}$C NMR (CD$_3$OD) $\delta$169.8 (2s), 155.9s, 143.6s, 142.2s, 135.7s, 124.7d, 124.6d, 123.6d, 121.2d, 115.5d, and 20.2 (2q); LRFABMS m/z 278 (M$^+$+1), 236, 194, 135, 119, and 103.

Example 4

Dihydrotubastrine 4 (Composition 4)

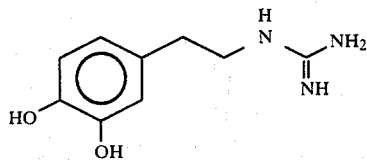

A mixture of (1) (30 mg), Pd/C (20 mg), and methanol (1 ml) acidified to pH 4.5 by adding 0.02% HCl was stirred with hydrogen under atmospheric pressure for 1 hr. After removing the catalyst by filtration the mixture was concentrated to give 30 mg (99.4%) of dihydrotubastrine (4) as colorless solid: mp 152°–7°; IR (film) 3350, 3180, 1650, 1620, 1520, 1440, 1350, 1280, 1190, and 1010 cm$^{-1}$; UV (MeOH) $\lambda_{max}$ 204 ($\epsilon$18700), 220 ($\epsilon$5800), and 280 nm ($\epsilon$2700); $^1$H NMR (CD$_3$OD) $\delta$6.65 (1H, d, J=7.8 Hz), 6.63 (1H, br s), 6.50 (1H, d, J=7.8 Hz), 3.31 (2H, t, J=6.6 Hz), and 2.65 (2H, t, J=6.6 Hz); $^{13}$C NMR (CD$_3$OD) $\delta$158.6s, 146.4s, 145.1s, 130.7s, 121.1d, 116.9d, 116.6d, 43.9t, and 35.2t.

Example 5

Pyrimidine derivative of dihydrotubastrine (Composition 5):

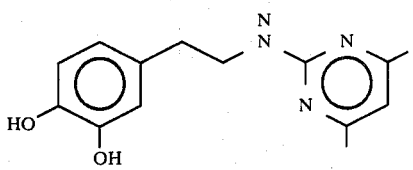

A mixture of (4) (27 mg), triethylamine (0.2 mL), pentane-2,4-dione (0.2 mL), and methanol (0.1 ml) in a sealed tube was heated at 80° C. for 3.5 hr. After removing the excess reagents in vacuo the residue was run on a short column of silica gel with ethyl acetate and finally purified by HPLC (RP-18, methanol-water 7:1) to give 23.5 mg (64.5%) of the pyrimidine 5. Recrystallization from heptane-ethyl acetate furnished colorless prisms, mp 164° C.; IR (CHCl$_3$) 3530, 3420, 2930, 1570, 1440, 1380, 1370, 1340, 1270, 1140, 1110, and 870 cm$^{-1}$; UV (MeOH)$\lambda_{max}$ 204 ($\epsilon$14200), 237 $\epsilon$13800), 285 ($\epsilon$5800), and 304 nm ($\epsilon$3900); $^1$H NMR (CDCl$_3$) $\epsilon$6.65 (1H, d, J=2 Hz), 6.58 (1H, d, J=8 Hz), 6.48 (1H, dd, J=8, 2 Hz), 6.31 (1H, s), 5.17 (br s, OH), 3.61 (2H, q, J=5.7 Hz), 2.74 (2H, t, J=6.2 Hz), and 2.29 (6H, s); $^{13}$C NMR (CDCl$_3$)$\epsilon$167.7s, 161.3 (2s), 144.7s, 143.1s, 130.8s, 120.5d, 115.3d, 114.8d, 109.8 (2d), 42.3t, 34.5t, and 23.5 (2q). HREIMS m/z 259.1323 (calcd for C$_{14}$H$_{17}$N$_3$O$_2$ 259.1321).

ANTIVIRAL ACTIVITIES OF THE COMPOSITIONS OF THE INVENTION

The following assay methods were utilized to demonstrate the in vitro antiviral effectiveness of compositions 1–5 as reported in Table 1.

ANTIVIRAL DISC ASSAY FOR HSV-1 AND VSV

A. Maintenance of Cell Cultures

1. Virus a. Both herpes simplex type 1 (HSV-1) and vesicular stomatitis virus (VSV) replicate in the CV-1 cell line. CV-1 is a fibroblast-like cell culture derived from primary African green monkey cells.

2. Growth of CV-1 Cells a. Seed 150 cm$^2$ tissue culture flasks each with 10×10$^6$ CV-1 cells in 40 ml of EMEM with 10% FBS (growth medium).

b. Seven days after seeding the flasks cell numbers should be approximately 40–50×10$_6$ cells. CV-1 cells have a doubling time of 72 hours based on these numbers.

3. Trypsinization a. Aseptically remove the medium.

b. Rinse cell sheet with 10 ml of $Ca^{++}$ and $Mg^{++}$ free Dulbecco's phosphate buffered saline or Pucks G saline at least twice.

c. Add 1.5 to 2.0 ml of trypsin -EDTA mixture.

d. Incubate flask at room temperature or at 37° C. with occasional rocking until the cells detach from the flask (about 15–30 min). Cells maintained on calf serum detach from the plastic at a faster rate than those held on fetal bovine serum (FBS).

e. Shake flask.

f. Add 10 ml EMEM growth medium and break up cell clumps with pipetting.

g. Count cells.

B. Preparation of plates for viral assays

1. Cell Concentration a. Dilute the cells with EMEM to $4 \times 10''$ cells/ml.

b. Seed 24 well trays with 0.5 ml per well. Cell concentration per well is $2 \times 10^5$ cells.

c. Incubate at 37° C. with 5% $CO_2$.

d. The wells can be used over the next several days beginning the day after seeding (preferably 2,3, or 4).

C. Assay of HSV-1 and VSV in CV-1 cells

1. Infection of CV-1 cells in plates with virus.

a. Remove medium from wells.

b. Infect well with at least 25 and no more than 80 plaque forming units (PFU) of virus.

c. Incubate infected cells at 37° C. for 1.5 hours.

d. Pour off supernatant at end of incubation period.

e. Add 0.5 ml of methylcellulose overlay medium (MCO).

(1) MCO is a maintenance medium without phenol red made with 1% 4000 centipoise methylcellulose. FBS is used at 5% level.

2. Drug Evaluation a. For drug evaluation wet filter paper discs (6 mm diameter) with approximately 0.02 ml of marine extract or test compound.

(1) Allow solvent to evaporate for 20 to 30 minutes at room temperature.

(2) Place discs in the well containing CV-1 cells, virus, and MCO.

b. Incubate tissue culture plates for 48 hours at 37° C.

c. After 48 hours place 0.5 ml NRMCO on each well.

(1) NRMCO is a maintenance overlay medium without phenol red containing 0.1 mg neutral red dye per ml and 2% 15 centipoise methylcellulose.

d. Incubate plates at 37° C. and read the following day.

(1) Antiviral activity should be observed from two parameters. One is actual reduction in the number of plaques and two is the diminution in plaque diameter.

ANTIVIRAL ASSAY FOR MOUSE CORONAVIRUS A-59

A. Cell culture

1. NCTC clone 1469 is a derivative of mouse liver.

2. ATCC No. CCL $9.1_3$ freeze 2518, passage no. 16, frozen November 1980 at $2.4 \times 10^3$.

3. Received January, 1985, and reconstituted March, 1985.

4. Frozen in liquid nitrogen and reconstituted July, 1985.

5. Assigned log number HB/SP 16.

B. Maintenance of cell culture

1. Trypsinization a. Aseptically remove the medium.

b. Rinse cell sheet with 10 ml of $Ca^{++}$ and $Mg^{++}$ free phosphate buffered saline.

c. Add 4 ml of trypsin-EDTA mixture to a 150 cm° flask.

d. Leave for one minute or less and then shake flask.

e. Add 10 ml of growth medium and break up cell clumps with pipetting.

f. Count cells.

2. Subcultures for maintenance of cells for assays.

a. Seed 150 $cm^2$ tissue culture flasks with $10 \times 10^6$ cells in 40 ml growth medium.

C. Virus

1. Mouse hepatitis virus strain MHV-A59 classified as a coronavirus.

2. ATCC No. 764.

3. Received January, 1985, passed in NCTC 1469 and assigned HB/SP 30 log number.

D. Preparation of plates for viral assays

1. Cell concentration a. Dilute the cells with growth medium between $5 \times 10_5$ and $7.5 \times 10^5$ cells per ml.

b. Seed 24 well trays with 1.0 ml per well.

E. Viral assay

1. Dilute drug or extract for test in the appropriate solvent.

2. Add 20 lambda to a 12 mm by 75 mm glass tube for a 16 mm test well.

3. Allow the solvent to evaporate under the laminar flow hood.

4. Dilute the MHV-A59 in Dulbecco's phosphate buffered saline with $Ca^{++}$ and $Mg^{++}$ to the appropriate predetermined dilution for the lot number currently in use. Normally the dilution of virus in a titration which gives a 3+ to 4+ CPE in 24 hours is the dilution used in this assay.

5. Remove medium from wells of 24 well plate containing NCTC 1469 cells seeded 24 earlier.

6. Add 200 lambda of diluted virus to each test well. Add PBS to control wells.

7. Incubate cells and virus for 1 hour at 37° C.

8. Pour off supernatant at end of incubation period.

9. To each glass tube add 10 lambda of dimethyl sulfoxide (DMSO).

10. Add 1 ml of maintenance medium to each glass tube.

11. Pour the contents of the glass tube into the corresponding well of the tissue culture plate.

12. Incubate infected cells at 37° C. and read the following day.

13. At twelve hours areas of cell fusion are quite apparent and can be detected both visually and microscopically.

14. At 24 hours the CPE is extensive and on stained plates the difference between activity and none is apparent from visual examination.

15. To stain plates discard medium and to each 16 mm well add 200 lambda of methylene blue stain or other appropriate stain.

16. Leave the stain on the cell sheet for 30 minutes or more.

17. Pour off the stain and wash plates in tap water until the water is clear.

18. Allow plates to dry. Plates can be kept as a permanent cord for the experiment.

SCORING ANTIVIRAL DRUG ACTIVITY (a) Antiviral activity is scored from 0 to +++.
+++ = complete inhibition of plaque formation
++ = partial inhibition
+ = partial inhibition
0 = no protection (b) Cytotoxicity
0 = no visual or microscopic cytotoxicity
16 = Complete cell destruction
8, 10, 12, 14 = partial cytotoxicity

TABLE 1

| Composition | Dose (μg/well) | VSV cyt | VSV av | HSV-1 cyt | HSV-1 av | MHV-A59 cyt | MHV-A59 av |
|---|---|---|---|---|---|---|---|
| 1 | 200 | 0 | +++ | 0 | +++ | | |
| | 100 | 0 | + | 0 | +++ | | |
| | 50 | 0 | − | 0 | + | 0 | − |
| | 25 | | | 0 | +/− | 0 | − |
| 2 | 120 | 0 | − | 0 | + | | |
| | 60 | 8 | − | 0 | +/− | 0 | − |
| | 6 | 0 | − | 0 | − | 0 | − |
| 3 | 120 | 0 | + | 0 | ++ | 0 | +/− |
| | 60 | 0 | +/− | 0 | + | 0 | − |
| | 6 | 0 | − | 0 | − | 0 | − |
| 4 | 120 | 0 | +/− | 0 | +++ | | |
| | 60 | 0 | − | 0 | − | 0 | − |
| | 6 | 0 | − | 0 | − | 0 | − |
| 5 | 120 | 16 | | 14 | +++ | | |
| | 60 | 8 | − | 8 | ++ | 0 | +++ |
| | 6 | 0 | − | 0 | − | 0 | +/− |

The results in Table 1 indicate that the compositions of the invention as represented by compositions 1–5 are effective for controlling VSV, HSV-1 and MHV-A59 viruses, in vitro, in concentrations as little as 6 μg/well. The results are indicative of the utility of the compositions of formulae I–VI to control viruses in hosts both animal and plant and control the diseases caused thereby.

The scope of the present invention is not limited by the description, examples, and suggested uses herein and modifications can be made without departing from the spirit of the invention. For example, it may be noted that other derivatives of the compositions of examples 1–5 such as a fluorinated derivative may possess antiviral activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A compound according to the formula:

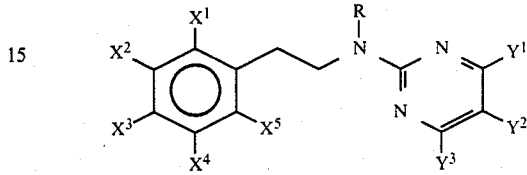

wherein R is is a hydrogen, hydroxyl, C1-5 alkanoyl, or C1-5 alkyl group; $X^{1-5}$ and $Y^{1-3}$ are the same or different and are hydrogen, halogen, nitro, hydroxyl, C1-5 alkoxy, C1-5 alkanoyloxy, thiol, C1-5 alkylthiol, amino, mono C1-5 alkylamino, di C1-5 alkylamino, C1-5 alkanoylamino, hydroxysulfonyl, aminosulfonyl, or C1-5 alkylsulfonyl groups.

2. A compound according to the formula:

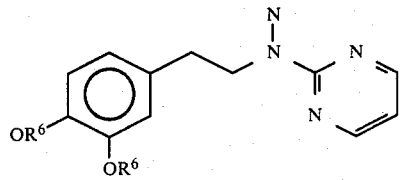

wherein $R^6$ are the same or different and are hydrogen or acetyl groups.

3. A compound of claim 1 that is substantially pure.

4. A compound of claim 2 that is substantially pure.

5. A pharmaceutical composition comprising, as an active ingredient, an effective antiviral amount of one or more of the compounds of claim 1 and a non-toxic pharmaceutically acceptable carrier or diluent.

6. A pharmaceutical composition comprising, as an active ingredient, an effective antiviral amount of one or more of the compounds of claim 2 and a non-toxic pharmaceutically acceptable carrier or diluent.

* * * * *

UNITED STATES PATENT AND TRADEMARK OFFICE
CERTIFICATE OF CORRECTION

PATENT NO. : 4,772,609
DATED : September 20, 1988
INVENTOR(S) : Tatsuo Higa and Ryuichi Sakai It is certified that error appears in the above—identified patent and that said Letters Patent is hereby corrected as shown below:

The formula in column 8 of the patent should read:

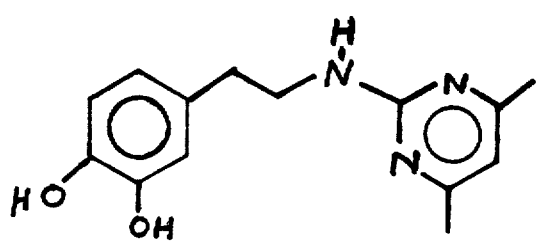

The formula in claim 2 should read:

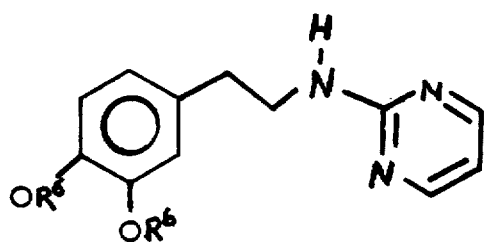

Signed and Sealed this

Seventh Day of February, 1989

Attest:

DONALD J. QUIGG

Attesting Officer

Commissioner of Patents and Trademarks